Figure 1:
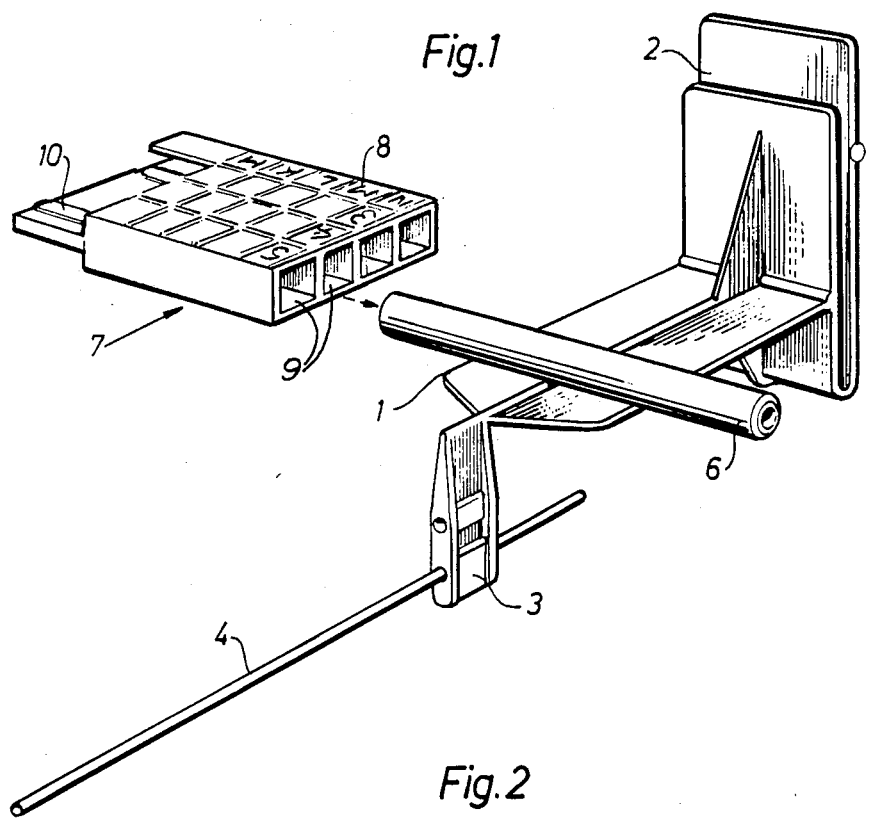

United States Patent [19]

Lindén

[11] Patent Number: 4,633,493
[45] Date of Patent: Dec. 30, 1986

[54] DENTAL INSTRUMENT FOR OPTIMAL POSITIONING OF AN X-RAY FILM SUPPORT, ESPECIALLY FOR USE IN THE X-RAYING OF FRONT TEETH

[76] Inventor: Enok S. R. Lindén, Teatergatan 4, S-582 22 Linköping, Sweden

[21] Appl. No.: 661,756

[22] Filed: Oct. 17, 1984

[30] Foreign Application Priority Data

Oct. 27, 1983 [SE] Sweden .............................. 83059105

[51] Int. Cl.⁴ .......................... G03B 42/02; A61B 6/14
[52] U.S. Cl. ..................................... 378/168; 378/170
[58] Field of Search ............................... 378/168–170, 378/205, 191

[56] References Cited

U.S. PATENT DOCUMENTS

| | | | |
|---|---|---|---|
| 2,082,793 | 6/1937 | De Weal | 378/170 |
| 2,123,210 | 7/1938 | Schantz | 378/170 |
| 2,525,959 | 10/1950 | Shapiro | 378/170 |
| 3,003,062 | 10/1961 | Updegrave | 378/170 |
| 4,295,050 | 10/1981 | Linden | 378/170 |
| 4,507,798 | 3/1985 | Welander | 378/168 |
| 4,538,292 | 8/1985 | Linden | 378/170 |
| 4,554,676 | 11/1985 | Maldonado et al. | 378/170 |

Primary Examiner—Craig E. Church
Assistant Examiner—Charles Wieland
Attorney, Agent, or Firm—Sughrue, Mion, Zinn, Macpeak and Seas

[57] ABSTRACT

The invention relates to a dental instrument for optimal positioning of an X-ray film support in the X-raying of teeth, especially front teeth, or adjacent tissues. The instrument comprises a bridge having at its one end which is located in the patient's oral cavity inside the subject to be X-rayed a holder keeping the film positioned perpendicularly to the longitudinal axis of the bridge and means receiving an alignment rod which is parallel to the longitudinal axis of the bridge and which projects outside the oral cavity whereby the optical axis of the X-ray camera can be positioned relatively the rod and hence relatively the film. The instrument is improved by means of a transverse support arm connected to the bridge and adapted to be held pressed between the teeth in the upper and lower jaws permitting rotation of the film holder around the geometric longitudinal axis of the support arm. The end portions of the arm are connectable to bite block means permitting rotation of the device around the longitudinal axis of the arm.

3 Claims, 4 Drawing Figures

DENTAL INSTRUMENT FOR OPTIMAL POSITIONING OF AN X-RAY FILM SUPPORT, ESPECIALLY FOR USE IN THE X-RAYING OF FRONT TEETH

A prior art film support device to be used by dentists when X-raying teeth comprises a plate-like portion having at its inner end a holder retaining the film. The device does also comprise means holding an aligning rod in a position in which the longitudinal axis of the rod is parallel to that of the plate-like portion. When the film is exposed, the outer end of that portion is located outside the teeth. It has markings which give information about the position of the film relatively the subject in said longitudinal axis direction. Further, the device comprises an arm which extends in the transverse direction of the plate-like portion, is co-planar therewith and provided with markings which, in the longitudinal direction of the arm, show the position of the film. Such a device is disclosed in my Swedish Pat. No. 7901788-5, Publication No. 423 484.

In the description of that Patent there is also mentioned that a correct orientation of the object of the X-ray camera relatively the film requires that two conditions must be satisfied. The first one is that the optical longitudinal axis of the camera object passes as exactly as possible through the center of the subject to be X-rayed, usally a tooth. The second condition is that this longitudinal axis should be perpendicular to either the plane of the film or to the bisector of the angle defined between that plane and the geometric longitudinal axis of the tooth. The two alternative ways of satisfying the second condition are referred to as the paralleling technique and the bisecting technique, respectively. The last-mentioned technique could be considered an "emergency" solution, adhered to when it is not possible to use the paralleling technique, the only one yielding optimized conditions for a correct picture.

The possibility of achieving a correct positioning of the film is, in addition to the structural and functional properties of the film support, dependent of two further factors. The one factor concerns the anatomy of the oral cavity or, simpler put, the space available for the film. The second factor is a function of the exact position along the row of teeth at which the exposure shall take place. The anatomical conditions vary substantially, between different individuals and in different parts of the oral cavity of any given individual. Those differences between teeth, occupying different positions in the row of teeth, which are relevant in this context are due to the different shapes of the chewing surfaces. The molars have very large chewing surfaces, whereas the front teeth have a chisel-like profile. As far as the canine teeth are concerned the conditions will be something between those two extremes.

Somewhat diagrammatically the difference here discussed may be described in the following way. When the teeth are clenched, there will be an extended surface contact between the molars but only line contact in the front region. This means that, when a film support according to the prior art is used, said plate-like portion will get a stable support and hence be securely held between two molars whereas, on the other hand, when it is positioned between the narrow edges of two front teeth, it assumes an instable position. The instability results in that also a very insignificant change of the contact pressure between the two jaws tend to tilt the plate so that the positioning made by the dentist is lost. However, it is still more usual that, due to the anatomical conditions in the oral cavity, more precisely the small height thereof immediately behind the front teeth, the dentist is forced already from the outset to place the film support in such a position that the plane of the film will form a substantial angle with the longitudinal axis of the tooth to be X-rayed or, differently put, it is absolutely impossible to use the paralleling technique.

Figure 2:
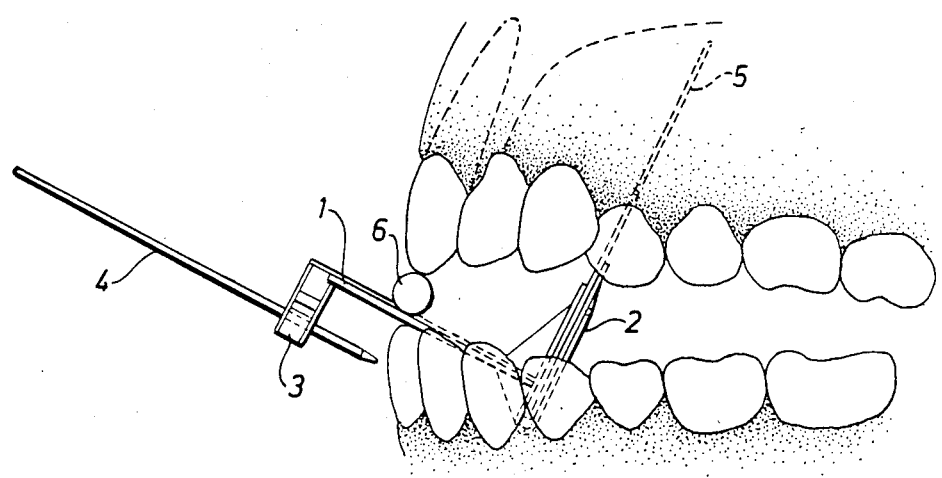
Figure 3:
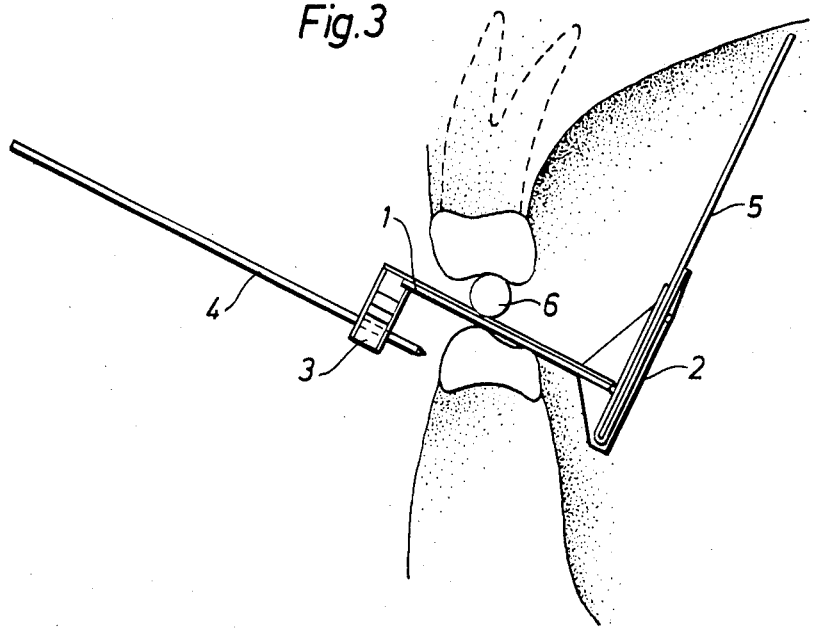
Figure 4:
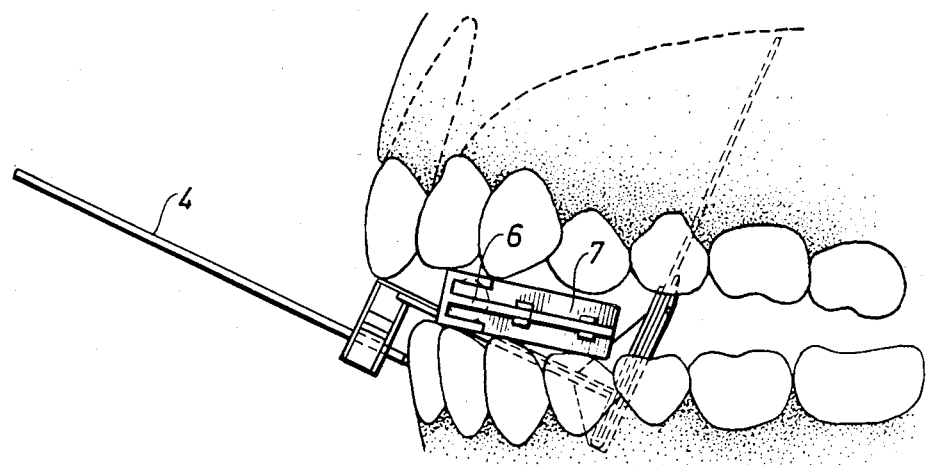

The object of the invention is to provide an X-ray film support for use in dentistry in which the limitations and drawbacks above mentioned are as far as possible eliminated. This means that the device shall, at least in the majority of cases, permit use of the advantageous paralleling technique also when front teeth are to be X-rayed. However, it should already here by emphasized that the field of use of the device is not at all limited to the front region of the oral cavity. Just the other way around, it is possible to use it also when X-raying molars and premolars. The characteristics of the invention are set out in the claims and two embodiments thereof will now be described, reference being made to the accompanying drawing, in which:

FIG. 1 is a perspective view of a film support according to the first embodiment;

FIG. 2 does in a diagrammatical lateral view show a device according to FIG. 1 positioned for X-ray photography of a front tooth in the upper jaw;

FIG. 3 corresponds to FIG. 2 but illustrates the use of the device for X-raying a premolar; and FIG. 4 does anatomically correspond to FIG. 2 but illustrates a device according to the second embodiment.

The combined film alignment and support device according to the invention does substantially consist of a bridge 1 which at its inner end, in relation to the oral cavity, has a transverse film holder 2. The latter does in a manner known per se consist of two parallel plates integral at their one ends. The film 5 is mounted in the slot defined between them as shown in FIGS. 2–4. At its opposite end which, during use of the device is located outside the oral cavity, bridge 1 is integral with a flange 3 having a through hole for an alignment rod 4.

To the extent so far described the device is previously known. However, according to the invention, bridge 1 is provided with a transverse support arm 6 which exerts two functions. The one function is to give support, the other to make it possible to rotate all of the device around the longitudinal axis of the arm. Such rotation may take place with direct or indirect contact between the support arm and the teeth which will be explained below.

In FIG. 2 the device has been located so that support arm 6, which according to this embodiment is of circular cross-section, holds film 5 positoned for X-raying of a front teeth section. The patient keeps his front and/or canine teeth pressed against arm 6. Thanks to the fact that arm 6 extends at both sides of bridge 1 lateral stability is achieved so that the film support, and hence the film, is prevented from tilting in the last-mentioned direction. Thanks to the fact that the teeth are in contact with arm 6 both from above and from below the dentist may conveniently select a suitable angle of tilt so that film 5 will be positioned parallel to the longitudinal axis of the tooth to be X-rayed. Differently put, he can use the advantageous paralleling technique also when X-raying front teeth.

According to FIG. 3 support arm 6 is instead located between premolars, i.e. teeth having sequence numbers 4 and 5. Even if, admittedly, the disadvantages of prior art film alignment and support devices are less pronounced in the X-raying of teeth within that region, FIG. 3 does clearly illustrate that at the dentist's disposal is here the same rotation possibility as according to FIG. 2. In addition thereto it appears from FIG. 3 that the stability against unintentional displacement movements is also improved.

In the embodiment illustrated in FIG. 4 the device shown in FIGS. 1-3 has been supplemented with two wing-like bite blocks 7-the detailed structure of which is shown in FIG. 1. Those bite blocks can be rotated round arm 6. The corresponding rotatability has been achieved in the way that the ends of arm 6 protrude into channels 9 opening in the end surfaces of the bite blocks. The use of such a block, at the one or at both ends of arm 6 as determined by the local conditions, results in that the transverse arm will no longer be in direct contact with the chewing surfaces of the teeth. These surfaces will instead contact the top and bottom sides of the blocks which thereby act as "bearings" for the arm. This improves the stability but, in addition thereto, it gives a further advantage. At subsequent treatments of the patient the dentist has the advantage that, when he wants to repeat his X-raying of a given subject, he can place the film in exactly the same position relatively that subject as it assumed at the first exposure. This is achieved thanks to the presence on bite block 7 of markings 8, the positions of which relatively the teeth are recorded by the dentist in connection with the first exposure. Bite blocks 7 also have ribs or grooves 10, or both, which make it possible to join several blocks and in that way further to increase the stabilizing surface by contact with more teeth.

The presence of several channels 9 in bite block 7, according to the embodiment of FIG. 1 four such channels, makes it possible to locate film holder 2 and film 5 in a position that far into the oral cavity which, in each individual case, yields an optimum result with regard to the position of the subject and to the anatomy of the oral cavity.

Finally, it should be underlined that the two embodiments of the invention here described and illustrated are only intended to exemplify the generic inventive concept. The latter is based on the realization that it is possible, by providing the device with a transverse arm, to make it rotatable in a vertical plane. The result thereof is that the patient can, without any difficulty at all, keep the film in a fixed position during the time required between positioning and exposure. When front teeth are X-rayed the transverse arm 6, which may have any suitable cross-section and shape, will as a rule have its projecting ends resting in the recesses formed between two adjacent teeth which gives the "hinge" effect aimed at. In embodiments comprising one or more bite blocks there is attained an absolute safety against unintentional movement of the film out of its selected position, the only requirement being that the patient should keep his teeth firmly pressed against the blocks-but he may well vary that pressure. It follows therefrom that those advantageous effects may be realized also in devices the various components of which have other shapes or proportions than those here illustrated. By way of example, support arm 6 may be tubular and adapted to receive corresponding pivots on bite blocks 7.

What is claimed is:

1. A dental instrument for positioning an X-ray film in the X-raying of teeth, especially front teeth, comprising:
   (a) an elongate planar bridge member (1) configured to be partially inserted into a patient's oral cavity,
   (b) a film holder (2) disposed on an inner end of the bridge member for removably mounting an X-ray film perpendicular to a longitudinal axis of the bridge member,
   (c) an X-ray camera alignment rod (4),
   (d) means (3) disposed on an outer end of the bridge member for mounting the alignment rod parallel to and offset from the bridge member axis such that the alignment rod extends outwardly from the oral cavity,
   (e) an elongate support arm (6) rigidly mounted to an intermediate portion of the bridge member, transverse to the longitudinal axis thereof, and having opposite ends extending outwardly from opposite sides of the bridge member, said support arm being:
      (1) positioned on the bridge member so as to be clamped between teeth in the upper and lower jaw of the patient in such a manner as to enable a limited rotation of the film holder about a longitudinal axis of the support arm, and
      (2) sufficiently spaced from the film holder along the longitudinal axis of the bridge member to extend the holder into the oral cavity a sufficient distance to enable a film mounted in the holder to be oriented parallel to a longitudinal axis of a tooth being X-rayed, and
   (f) bite block means (7) optionally engageable with an end of the support arm for permitting rotation of the support arm about its longitudinal axis, said bite block means having a plurality of spaced support arm engagement positions to enable the distance within the oral cavity between the film holder (2) and the tooth being X-rayed to be selectively varied.

2. An instrument as claimed in claim 1, wherein the support arm (6) is of circular cross-section.

3. An instrument as claimed in claim 6, wherein said bite block means (7) is provided with markings (8) indicating said distance.

* * * * *